United States Patent
Schwalge et al.

[11] Patent Number: 5,939,454
[45] Date of Patent: Aug. 17, 1999

[54] FUNGICIDAL MIXTURES OF AN OXIME ETHER CARBOXYLIC ACIT AMIDE WITH A DITHIOCARBAMATE

[75] Inventors: Barbara Schwalge, Heidelberg; Ruth Müller, Friedelsheim; Herbert Bayer; Hubert Sauter, both of Mannheim; Eberhard Ammermann, Heppenheim; Gisela Lorenz, Hambach; Siegfried Strathmann, Limburgerhof, all of Germany

[73] Assignee: BASF Akdtiengesellschaft, Ludwigshafen, Georgia

[21] Appl. No.: 09/012,000

[22] PCT Filed: Aug. 5, 1996

[86] PCT No.: PCT/EP96/03440

§ 371 Date: Jan. 20, 1998

§ 102(e) Date: Jan. 20, 1998

[87] PCT Pub. No.: WO97/06683

PCT Pub. Date: Feb. 27, 1997

[30] Foreign Application Priority Data

Aug. 17, 1995 [DE] Germany ............... 19530/69

[51] Int. Cl.$^6$ ............ A01N 37/18; A01N 47/10
[52] U.S. Cl. ............ 514/491; 514/476; 514/619
[58] Field of Search ............ 514/619, 476, 514/491

[56] References Cited

U.S. PATENT DOCUMENTS

| | | | |
|---|---|---|---|
| 2,457,674 | 12/1948 | Heuberger | 167/22 |
| 2,504,404 | 4/1950 | Flenner | 162/22 |
| 3,248,400 | 4/1966 | Flieg et al. | 260/313 |
| 3,379,610 | 4/1968 | Lyon | 167/22 |
| 5,500,446 | 3/1996 | Wingert et al. | 514/483 |

FOREIGN PATENT DOCUMENTS

| | | |
|---|---|---|
| 2132048 | 3/1995 | Canada . |
| 645 089 | 3/1995 | European Pat. Off. . |
| 741 970 | 11/1996 | European Pat. Off. . |
| 2 279 568 | 1/1995 | United Kingdom . |
| 95/15083 | 6/1995 | WIPO . |
| 95/18789 | 7/1995 | WIPO . |
| 95/21154 | 8/1995 | WIPO . |

OTHER PUBLICATIONS

Pesticide Sci., vol. 44, No. 1, May 1995 pp. 77–79.
Research Disc. Jun. 1992, No. 338.
Res. Disc. Apr. 1993, No. 348.

*Primary Examiner*—Allen J. Robinson
*Attorney, Agent, or Firm*—Keil & Weinkauf

[57] ABSTRACT

A fungicidal mixture comprises
a) an oxime ether carboxamide of the formula I

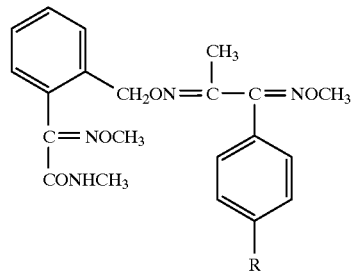

where R is hydrogen or halogen
and
b) a dithiocarbamate (II) selected from the group consisting of
manganese ethylenebis(dithiocarbamate) (zinc complex) (IIa),
manganese ethylenebis(dithiocarbamate) (IIb),
zinc ammoniate ethylenebis(dithiocarbamate) (IIc) and
zinc ethylenebis(dithiocarbamate) (IId)
in a synergistically active amount.

10 Claims, No Drawings

FUNGICIDAL MIXTURES OF AN OXIME ETHER CARBOXYLIC ACIT AMIDE WITH A DITHIOCARBAMATE

This application is a 371 of PCT/EP96/03440, filed Aug. 05, 1996.

The present invention relates to a fungicidal mixture which comprises
a) an oxime ether carboxamide of the formula I

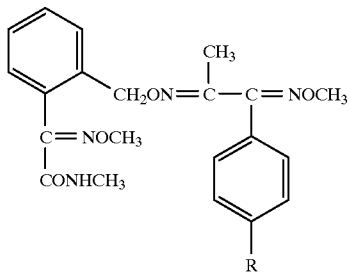

where R is hydrogen or halogen
and
b) a dithiocarbamate (II) selected from the group consisting of
manganese ethylenebis(dithiocarbamate) (zinc complex) (IIa),
manganese ethylenebis(dithiocarbamate) (IIb),
zinc ammoniate ethylenebis(dithiocarbamate) (IIc) and
zinc ethylenebis(dithiocarbamate) (IId)
in a synergistically active amount.

Moreover, the invention relates to methods of controlling harmful fungi using mixtures of the compounds I and II and to the use of the compounds I and of the compounds II for the preparation of such mixtures.

The compounds of the formula I, their preparation and their action against harmful fungi are disclosed in the literature (WO-A 95/18,789).

Also disclosed are the dithiocarbamates II (IIa: common name: mancozeb, U.S. Pat. No. 3,379,610; IIb: common name: maneb, U.S. Pat. No. 2,504,404; IIc: former common name: metiram, U.S. Pat. No. 3,248,400; IId: common name: zineb, U.S. Pat. No. 2,457,674), their preparation, and their action against harmful fungi.

It was an object of the present invention to provide mixtures which have an improved action against harmful fungi combined with a reduced total amount of active ingredients applied (synergistic mixtures), with a view to reducing the rates of application and to improving the spectrum of action of the known compounds.

Accordingly, we have found that this object is achieved by the mixtures defined at the outset. Moreover, we have found that better control of the harmful fungi is possible by applying the compounds I and the compounds II simultaneously together or separately or by applying the compounds I and the compounds II in succession than when the individual compounds are used.

R in formula I is hydrogen or a halogen atom such as fluorine, chlorine, bromine or iodine, especially hydrogen, fluorine or chlorine, in particular hydrogen or fluorine.

In relation to the C=N double bond, the compounds of the formula I can be present in the E or the Z configuration (in relation to the carboxylic acid function). Accordingly, they can be used in the mixture according to the invention in each case either in the form of a pure E or Z isomer or else in the form of an E/Z isomer mixture. The E/Z isomer mixture or the E isomer is preferably used, the E isomer being especially preferred.

The C=N double bonds of the oxime ether groups in the side chain of the compounds I can exist in each case in the form of a pure E or Z isomer or in the form of E/Z isomer mixtures. The compounds I can be used in the mixtures according to the invention as isomer mixtures or else as the pure isomers. With a view to their use, compounds I which are particularly preferred are those where both oxime ether groups in the side chain are in the E configuration (E/E).

Due to the basic character of the NH group, the compounds I are capable of forming adducts or salts with inorganic or organic acids or with metal ions.

Examples of inorganic acids are hydrohalic acids such as hydrofluoric acid, hydrochloric acid, hydrobromic acid and hydriodic acid, sulfuric acid, phosphoric acid and nitric acid.

Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or aryldisulfonic acids (aromatic radicals, such as phenyl and naphthyl, which have attached to them one or two sulfo groups), alkylphosphonic acids (phosphonic acids having straight-chain or branched alkyl radicals of 1 to 20 carbon atoms), arylphosphonic acids or aryldiphosphonic acids (aromatic radicals, such as phenyl and naphthyl, which have attached to them one or two phosphoric acid radicals), it being possible for the alkyl or aryl radicals to have attached to them further substituents, eg. p-toluenesulfonic acid, salicylic acid, p-aminosalicylic acid, 2-phenoxybenzoic acid, 2-acetoxybenzoic acid etc.

Suitable metal ions are, in particular, the ions of the elements of the second main group, in particular calcium and magnesium, of the third and fourth main group, in particular aluminum, tin and lead, and of the first to eighth sub-group, in particular chromium, manganese, iron, cobalt, nickel, copper, zinc and others. Especially preferred are the metal ions of the elements of the sub-groups of the fourth period. The metals can exist in the various valencies which they can assume.

When preparing the mixtures, it is preferred to employ the pure active ingredients I and II, with which further active ingredients against harmful fungi or other pests, such as insects, arachnids or nematodes, or else herbicidal or growth-regulating active ingredients or fertilizers can be admixed, if so required.

The mixtures of the compounds I and II, or the simultaneous joint or separate use of the compounds I and II, are distinguished by outstanding action against a wide spectrum of phytopathogenic fungi, in particular from the classes of the Ascomycetes and Basidiomycetes. Some of them act systemically and can therefore be employed as foliar- and soil-acting fungicides.

They are especially important for controlling a large number of fungi in a variety of crop plants, such as cotton, vegetable species (eg. cucumbers, beans and cucurbits), barley, grass, oats, coffee, maize, fruit species, rice, rye, soya, grapevine, wheat, ornamentals, sugar cane, and a variety of seeds.

They are particularly suitable for controlling the following phytopathogenic fungi: *Erysiphe graminis* (powdery mildew) in cereals, *Erysiphe cichoracearum* and *Sphaerotheca fuliginea* in cucurbits, *Podosphaera leucotricha* in apples, Puccinia species in cereals, Rhizoctonia species in cotton and lawns, Ustilago species in cereals and sugar cane, *Venturia inaequalis* (scab) in apples, Helminthosporium species in cereals, *Septoria nodorum* in wheat, *Botrytis cinerea* (gray mold) in strawberries and grapevines, cercospora arachidicola in groundnuts, *Pseudocercosporella herpotrichoides* in wheat and barley, *Pyricularia oryzae* in rice, *Phytophthora infestans* in potatoes and tomatoes, *Pseudoperonospora cubense* in cucurbits, *Plasmopara viticola* in grapevines, Alternaria species in vegetables and fruit, and Fusarium and Verticillium species.

Furthermore, they can be used in the protection of materials (eg. in the protection of wood), for example against *Paecilomyces variotii*.

The compounds I and II can be applied simultaneously together or separately or in succession, the sequence, in the case of separate application, generally not having any effect on the result of the control measures.

The compounds I and II are usually used in a weight ratio of 200:1 to 0.1:1, preferably 100:1 to 1:1, in particular 50:1 to 5:1 (II:I).

The application rates of the mixtures according to the invention are, in the case of the compounds I, from 0.005 to 0.5 kg/ha, preferably 0.01 to 0.5 kg/ha, in particular 0.01 to 0.3 kg/ha, depending on the nature of the desired effect. Correspondingly, in the case of the compounds II, the application rates are from 0.1 to 10 kg/ha, preferably 0.5 to 5 kg/ha, in particular 1 to 4 kg/ha.

For seed treatment, the application rates of the mixture are generally from 0.001 to 100 g/kg of seed, preferably 0.01 to 50 g/30 kg, in particular 0.01 to 10 g/kg.

If phytopathogenic harmful fungi are to be controlled, the separate or joint application of the compounds I and II or of the mixtures of the compounds I and II is effected by spraying or dusting the seeds, the plants or the soils before or after sowing of the plants, or before or after plant emergence.

The fungicidal synergistic mixtures according to the invention, or the compounds I and II, can be formulated for example in the form of ready-to-spray solutions, powders and suspensions or in the form of highly concentrated aqueous, oily or other suspensions, dispersions, emulsions, oil dispersions, pastes, dusts, materials for spreading or granules, and applied by spraying, atomizing, dusting, spreading or pouring. The use form depends on the intended purpose; in any case, it should guarantee as fine and uniform as possible a distribution of the mixture according to the invention.

The formulations are prepared in a manner known per se, eg. by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, lignosulfite waste liquors or methylcellulose.

Powders, materials for spreading and dusts can be prepared by mixing or jointly grinding the compounds I or II or the mixture of the compounds I and II with a solid carrier.

Granules (eg. coated granules, impregnated granules or homogeneous granules) are usually prepared by binding the active ingredient, or active ingredients, to a solid carrier.

Fillers or solid carriers are, for example, mineral earths, such as silica gel, silicas, silica gels, silicates, talc, kaolin, limestone, lime, chalk, bole, loess, clay, dolomite, diatomaceous earth, calcium sulfate, magnesium sulfate, magnesium oxide, ground synthetic materials, and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise 0.1 to 95% by weight, preferably 0.5 to 90% by weight, of one of the compounds I or II or of the mixture of the compounds I and II. The active ingredients are employed in a purity of from 90% to 100%, preferably 95% to 100% (according to NMR or HPLC spectrum).

The compounds I or II, or the mixtures, or the corresponding formulations, are applied by treating the harmful fungi or the plants, seeds, soils, areas, materials or spaces to be kept free from them with a fungicidally active amount of the mixture, or of the compounds I and II in the case of separate application. Application can be effected before or after infection by the harmful fungi.

Examples of the synergistic action of the mixtures according to the invention against harmful fungi.

The fungicidal action of the compounds and of the mixtures was demonstrated by the following experiments:

The active ingredients, separately or together, were formulated as a 10% emulsion in a mixture of 70% by weight of cyclohexanone, 20% by weight of Nekanil® LN (Lutensol® AP6, wetting agent having emulsifying and dispersing action, based on ethoxylated alkylphenols) and 10% by weight of Emulphor® EL (Emulan® EL, emulsifier based on ethoxylated fatty alcohols) and diluted with water to give the desired concentration.

Evaluation was by determining the infected leaf areas in percent. These percentages were converted into degrees of action. The expected degrees of action of the mixtures of the active ingredients were determined using Colby's formula [R. S. Colby, Weeds 15, 20–22 (1967)] and compared with the observed degrees of action.

Colby's formula:

$$E = x + y - x \cdot y/100$$

E expected degree of action, expressed in % of the untreated control, when using the mixture of the active ingredients A and B at the concentrations a and b x degree of action, expressed in % of the untreated control, when using active ingredient A at a concentration of a y degree of action, expressed in % of the untreated control, when using active ingredient B at a concentration of b The efficacy (E) was calculated as follows using Abbot's formula:

$$E=(1-\alpha)\cdot 100/\beta$$

α corresponds to the fungal infection of the treated plants in % and

β corresponds to the fungal infection of the untreated (control) plants in %

A degree of action of 0 means that the infection level of the treated plants corresponds to that of the untreated control plants; a degree of action of 100 means that the treated plants were not infected.

The expected efficacies of the mixtures of the active ingredients were calculated using Colby's formula and compared with the observed efficacies.

Activity against *Phytopophthora infestans* (blight)

Leaves of tomato plants (cultivar "Große Fleischtomate") were first treated with the aqueous preparation of the active ingredients. After approxiamately 24 hours, the plants were infected with a zoospore suspension of *Phytophthora infestans*. The treated plants were subsuquently incubated for 6 days at 16–18° C. and a relative atmospheric humidity of 100%. The extent of the fungal development was subsuquently determined.

| Active ingredient | Rate of application [ppm] | Efficacy [%] |
|---|---|---|
| untreated | -/- | 0 |
| I.a | 8 | 0 |
|  | 4 | 0 |
|  | 2 | 0 |
|  | 1 | 0 |
| I.b | 8 | 5 |
|  | 4 | 5 |
|  | 2 | 0 |
|  | 1 | 0 |
| II.b | 80 | 0 |
|  | 40 | 0 |
|  | 20 | 0 |
| II.c | 80 | 50 |
|  | 40 | 40 |
|  | 20 | 5 |

| Active ingredients | Rate of application/ mixing ratio | Efficacy Observed | Caluclated |
|---|---|---|---|
| I.a + II.b | 8 + 80/1:10 | 40 | 0 |
|  | 4 + 40/1:10 | 30 | 0 |
|  | 8 + 80/1:10 | 90 | 50 |
|  | 4 + 40/1:10 | 75 | 40 |
| I.a + II.c | 2 + 20/1:10 | 75 | 5 |
|  | 8 + 40/1:5 | 60 | 40 |
|  | 4 + 20/1:5 | 60 | 5 |
|  | 8 + 80/1:10 | 80 | 5 |
|  | 4 + 40/1:10 | 80 | 5 |
| I.b + II.b | 2 + 20/1:10 | 60 | 0 |
|  | 8 + 40/1:5 | 70 | 5 |
|  | 4 + 20/1:5 | 40 | 5 |
|  | 8 + 80/1:10 | 95 | 53 |
|  | 4 + 40/1:10 | 93 | 43 |
| I.b + II.c | 8 + 40/1:5 | 65 | 53 |
|  | 4 + 20/1:5 | 75 | 43 |

We claim:

1. A fungicidal composition comprising
a) an oxime ether carboxamide of the formula I

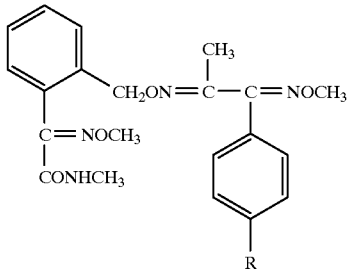

where R is hydrogen or halogen, and
b) a dithiocarbamate compound II selected from the group consisting of
   manganese ethylenebis(dithiocarbamate) (zinc complex) (IIa),
   manganese ethylenebis(dithiocarbamate) (IIb),
   zinc ammoniate ethylenebis(dithiocarbamate (IIc) and
   zinc ethylenebis(dithiocarbamate) (IId)
in a synergistically active amount.

2. The fungicidal composition defined in claim 1, comprising manganese ethylenebis(dithiocarbamate) (zinc complex) (IIa).

3. The fungicidal composition defined in claim 1, comprising manganese ethylenebis(dithiocarbamate) (IIb).

4. The fungicidal composition defined in claim 1, comprising zinc ammoniate ethylenebis(dithiocarbamate) (IIc).

5. The fungicidal composition defined in claim 1, comprising zinc ethylenebis(dithiocarbamate) (IId).

6. The fungicidal composition defined in claim 1, wherein the weight ratio of the compound II to the compound of the formula I is 200:1 to 0.1:1.

7. A method of controlling harmful fungi, which comprises treating the harmful fungi, their environment, or the plants, seeds, soils, areas, materials or spaces to be kept free from said fungi with a synergistically effective amount of the compound of the formula I as defined in claim 1 and the compound II as defined in claim 1.

8. The method defined in claim 7, wherein the compound of the formula I and the compound II are applied simultaneously together or separately, or in succession.

9. The method defined in claim 7, wherein from 0.005 to 0.5 kg/ha of the compound of the formula I are applied.

10. The method defined in claim 7, wherein from 0.1 to 10 kg/ha of the compound II are applied.

* * * * *

UNITED STATES PATENT AND TRADEMARK OFFICE
CERTIFICATE OF CORRECTION

PATENT NO.: 5,939,454

DATED: August 17, 1999

INVENTOR(S): SCHWALGE et al.

It is certified that error appears in the above-identified patent and that said Letters Patent is hereby corrected as shown below:

On the cover page, in the title, item [54], "ACIT" should be --ACID--.

On the cover page, item [73], "Georgia" should be --Germany--.

On the cover page, item [30], the priority document number should be --195 30 169--.

Signed and Sealed this

Eighteenth Day of January, 2000

*Attest:*

Q. TODD DICKINSON

*Attesting Officer*  *Commissioner of Patents and Trademarks*